(12) United States Patent
Shizuno et al.

(10) Patent No.: US 11,324,236 B2
(45) Date of Patent: May 10, 2022

(54) FUNCTIONAL FEED

(71) Applicant: IDEMITSU KOSAN CO., LTD., Chiyoda-ku (JP)

(72) Inventors: Yuji Shizuno, Chiyoda-ku (JP); Chie Hikita, Chiyoda-ku (JP); Yasuhiro Suzuki, Sendai (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 16/077,454

(22) PCT Filed: Feb. 10, 2017

(86) PCT No.: PCT/JP2017/004999
§ 371 (c)(1),
(2) Date: Aug. 11, 2018

(87) PCT Pub. No.: WO2017/138654
PCT Pub. Date: Aug. 17, 2017

(65) Prior Publication Data
US 2019/0069577 A1    Mar. 7, 2019

(30) Foreign Application Priority Data

Feb. 12, 2016   (JP) .............................. JP2016-024922

(51) Int. Cl.
| | | |
|---|---|---|
| A23K 50/75 | (2016.01) | |
| A23K 20/158 | (2016.01) | |
| A23K 20/111 | (2016.01) | |
| A61K 36/22 | (2006.01) | |
| A61K 31/05 | (2006.01) | |
| A61K 31/202 | (2006.01) | |

(52) U.S. Cl.
CPC ............ *A23K 50/75* (2016.05); *A23K 20/111* (2016.05); *A23K 20/158* (2016.05); *A61K 31/05* (2013.01); *A61K 31/202* (2013.01); *A61K 36/22* (2013.01)

(58) Field of Classification Search
None
See application file for complete search history.

(56) References Cited

U.S. PATENT DOCUMENTS

| | | | |
|---|---|---|---|
| 5,725,894 A | 3/1998 | Toyomizu et al. | |
| 6,379,694 B1 | 4/2002 | Hatano et al. | |
| 2008/0160000 A1* | 7/2008 | Motozono | A61K 31/05 424/93.45 |
| 2011/0177184 A1* | 7/2011 | Suzuki | A61K 36/22 424/776 |
| 2011/0250303 A1* | 10/2011 | Nagashima | A61K 31/05 424/769 |
| 2013/0224320 A1 | 8/2013 | Campmany | |
| 2015/0359831 A1* | 12/2015 | Campmany | A61K 36/22 424/769 |

FOREIGN PATENT DOCUMENTS

| | | | |
|---|---|---|---|
| CN | 104382970 | | 3/2015 |
| CN | 107205438 | | 9/2017 |
| CN | 104486943 B | * | 8/2018 |
| JP | 8-231410 A | | 9/1996 |
| JP | 2001-151675 A | | 6/2001 |
| JP | 2014-121331 A | | 7/2014 |
| JP | 2015-30717 | * | 2/2015 |
| JP | 2015-30717 A | | 2/2015 |
| WO | WO 2010/113886 A1 | | 10/2010 |
| WO | WO 2014122915 | * | 8/2014 |
| WO | WO 2015/056729 A1 | | 4/2015 |

OTHER PUBLICATIONS

CN104486943B https://patents.google.com/patent/CN104486943B/en?q=%22Production+score%22+(chicken+or+poultry)&oq=%22Production+score%22+and+(chicken+or+poultry).*
International Search Report dated Apr. 25, 2017 in PCT/JP2017/004999 filed Feb. 10, 2017.
Extended European Search Report dated Sep. 10, 2019 in Patent Application No. 17750375.2, 8 pages.
C. A. A. Lopez, et al., "Effects of Cashew Nut Shell Liquid (CNSL) on the Performance of Broiler Chickens" Arquivo Brasileiro de Medicina Veterinaria E Zootecnia—Brazilian Archive of Veterinary Medicine and Zootechny, vol. 64, No. 4, XP009515710, Jul. 31, 2012, pp. 1027-1035.
International Preliminary Report on Patentability and Written Opinion dated Aug. 23, 2018 in PCT/JP2017/004999.
Office Action dated May 19, 2021 issued in Chinese patent application No. 201780011002.2 with English Translation, 23 pages.

\* cited by examiner

*Primary Examiner* — Danah Al-Awadi
(74) *Attorney, Agent, or Firm* — Oblon, McClelland, Maier & Neustadt, L.L.P.

(57) ABSTRACT

The present invention provides a productivity enhancing agent, a wasting rate-reducing agent, an ameliorating agent for ascites, emaciation, or maldevelopment, and a prophylactic or therapeutic agent for inflammation or colibacillosis for use in poultry such as chickens for meat, which comprises unheated cashew nut shell liquid, heated cashew nut shell liquid, anacardic acid, cardanol, and/or cardol.

7 Claims, No Drawings

FUNCTIONAL FEED

TECHNICAL FIELD

The present invention relates to a productivity enhancing agent, an ameliorating agent for ascites, emaciation, or maldevelopment, a wasting rate-reducing agent, and a prophylactic or therapeutic agent for inflammation or colibacillosis for use in poultry, preferably in chickens for meat (broiler chickens), which comprises unheated cashew nut shell liquid, heated cashew nut shell liquid, anacardic acid, cardanol, and/or cardol, as well as relates to a feed for poultry, preferably for chickens for meat, using the same.

BACKGROUND ART

A key factor in enhancing the productivity of chickens for meat is to produce and ship more amount of meat per unit farming area. Although, to date, the general productivity and the meat productivity have already been largely enhanced not only by genetic breeding but also by vaccination and improvement of environment, further enhancement in productivity is being demanded.

There have been cases in which, to improve the productivity, chickens are fed with functional materials such as antioxidants or probiotics (for example, flavonoids, polyphenols, lactic acid bacteria, *Pseudomonas* bacteria, *Flavobacterium* bacteria), enzymes (for example, phytase, protease, CoQ), herbs (for example, *Verbena officinalis*, *Houttuynia cordata*, garlic powder, allspice, clove, other spices), amino acids (for example, L-glutamic acid), and monosaccharides, as well as are subjected to nutrition management (for example, vitamins B1 and E). In Japan, the "Poultry Slaughtering Business Control and Poultry Meat Inspection Act" has been enacted from the viewpoint of public health, which requires to perform antemortem and postmortem inspection of poultry on the external and internal surfaces of carcasses prior to delivery and, if any abnormality is found in the inspection, to waste either all or a part of the poultry products. Major causes of complete wasting include colibacillosis, ascites, emaciation or maldevelopment, inflammation, and the like. Thus, reduction of these conditions which cause 60 to 80 percent of complete wasting cases leads to further enhancement in productivity. Particularly, the incidence of colibacillosis tends to be decreased by using a specific vaccine against colibacillosis together with a herbal medicine (for example, sumac gallnut extract), a chicken egg antibody and an organic acid mixture, but colibacillosis still occurs at a high incidence in production sites of chickens for meat and thus a more useful countermeasure is demanded.

Patent Document 1 describes an ameliorating agent for coccidiosis (enteritis caused by *Eimeria* protozoan infection) in poultry including chickens for meat, such as broiler chicken, which is characterized by comprising cashew nut shell liquid and/or anacardic acids as an active ingredient/active ingredients.

Patent Document 2 describes a feed for poultry including chickens for meat, such as broiler chicken, to prevent and/or treat coccidiosis, which is characterized by comprising, as active ingredients, cashew nut shell liquid and/or anacardic acids as well as at least one selected from an organozinc compound, betaine and a *Bacillus* bacterium.

However, it was unknown that the administration of cashew nut shell liquid enabled to improve the productivity of poultry such as chickens for meat and to reduce the wasting rate after delivery and, furthermore, to reduce the incidence of colibacillosis or inflammation in poultry such as chickens for meat.

PRIOR ART DOCUMENTS

Patent Documents

Patent Document 1: Japanese Unexamined Patent Publication No. Hei8-231410
Patent Document 2: Japanese Unexamined Patent Publication No. 2001-151675

SUMMARY OF THE INVENTION

Problems to be Solved by the Invention

An object of the present invention is to enhance the productivity of poultry. Another object of the present invention is to reduce the wasting rate of poultry. Still another object of the present invention is to reduce the incidence of colibacillosis or inflammation in poultry.

Means for Solving the Problems

The inventors intensively studied to solve the above-described problems and consequently found that use of unheated cashew nut shell liquid, heated cashew nut shell liquid, anacardic acid, cardanol, and/or cardol was effective in poultry such as chickens for meat in improvement of the maturity rate, in improvement of the feed conversion rate, in improvement of the production index and reference value, and in reduction of the wasting rate due to colibacillosis, inflammation, ascites, emaciation, and maldevelopment. In this way, the inventors have completed the present invention.

The present invention is as described below.
(1) A productivity enhancing agent for poultry, comprising unheated cashew nut shell liquid, heated cashew nut shell liquid, anacardic acid, cardanol, and/or cardol (excluding an agent to enhance the productivity by ameliorating coccidiosis).
(2) A feed for poultry comprising the productivity enhancing agent according to (1).
(3) The feed according to (2), wherein unheated cashew nut shell liquid, heated cashew nut shell liquid, anacardic acid, cardanol, and/or cardol is present in the feed at a concentration of 0.0001 to 10.0% by mass.
(4) The feed according to (2) or (3), wherein the feed is a feed for the late fattening period.
(5) The feed according to any one of (2) to (4), wherein the poultry are chickens for meat.
(6) A method of enhancing the productivity of poultry, the method comprising providing the poultry with the feed according to any one of (2) to (4).
(7) The method according to (6), wherein the poultry are chickens for meat.
(8) The method according to (7), wherein the chicken for meat is a one- to seven-week-old chicken.
(9) A prophylactic or therapeutic agent for inflammation or colibacillosis in poultry, comprising unheated cashew nut shell liquid, heated cashew nut shell liquid, anacardic acid, cardanol, and/or cardol as an active ingredient.
(10) A method of preventing or treating inflammation or colibacillosis in poultry, the method comprising administering the poultry with unheated cashew nut shell liquid, heated cashew nut shell liquid, anacardic acid, cardanol, and/or cardol.

(11) A method of enhancing the productivity of poultry, the method comprising administering the poultry with a feed containing unheated cashew nut shell liquid, heated cashew nut shell liquid, anacardic acid, cardanol, and/or cardol at a concentration of 1 to 150 ppm.

(12) A wasting rate-reducing agent for poultry, comprising unheated cashew nut shell liquid, heated cashew nut shell liquid, anacardic acid, cardanol, and/or cardol.

(13) A method of reducing the wasting rate of poultry, the method comprising the step of administering the poultry with unheated cashew nut shell liquid, heated cashew nut shell liquid, anacardic acid, cardanol, and/or cardol.

(14) An ameliorating agent for ascites, emaciation, or maldevelopment in poultry, comprising unheated cashew nut shell liquid, heated cashew nut shell liquid, anacardic acid, cardanol, and/or cardol.

(15) A method of ameliorating ascites, emaciation, or maldevelopment in poultry, the method comprising the step of administering the poultry with unheated cashew nut shell liquid, heated cashew nut shell liquid, anacardic acid, cardanol, and/or cardol.

Effects of the Invention

Use of the productivity enhancing agent for poultry according to the present invention or the feed comprising the same enables to increase the productivity of poultry. Also, administration of the productivity enhancing agent for poultry according to the present invention or the feed comprising the same enables to decrease the number of fowls wasted due to, for example, colibacillosis, inflammation, ascites, emaciation, and maldevelopment, as compared with that in untreated fowls and thus to reduce the total wasting rate of poultry.

DETAILED DESCRIPTION OF THE INVENTION

The productivity enhancing agent and the wasting rate-reducing agent for poultry according to the present invention are characterized by comprising unheated cashew nut shell liquid, heated cashew nut shell liquid, anacardic acid, cardanol, and/or cardol.

Cashew nut shell liquid is an oily liquid contained in the nutshell of the cashew nut tree (*Anacardium occidentale* L.). Cashew nut shell liquid contains, as its components, anacardic acid, cardanol and cardol. In general, anacardic acid is converted into cardanol by heat treatment. Cashew nut shell liquid (unheated) extracted by pressing cashew nut shells comprises 55 to 80% by mass of anacardic acid, 5 to 20% by mass of cardanol and 5 to 30% by mass of cardol, as described in J. Agric. Food Chem. 2001, 49, 2548-2551. Heat treatment of cashew nut shell liquid at a temperature of not lower than 70° C., preferably not lower than 130° C., causes anacardic acid, a main component of cashew nut shell liquid, to be decarboxylated and converted into cardanol, and the obtained heated cashew nut shell liquid comprises 0 to 10% by mass of anacardic acid, 55 to 80% by mass of cardanol and 5 to 30% by mass of cardol. Storage of cashew nut shell liquid at room temperature (20° C.) for about one year or longer may cause anacardic acid, a main component of cashew nut shell liquid, to be decarboxylated and converted into cardanol and, in this case, the obtained cashew nut shell liquid comprises 0 to 40% by mass of anacardic acid, 30 to 80% by mass of cardanol and 5 to 30% by mass of cardol.

Cashew nut shell liquid can be obtained as a plant oil extracted by pressing cashew nut shells. Moreover, cashew nut shell liquid can also be obtained, for example, by solvent extraction of cashew nut shells. Furthermore, cashew nut shell liquid can be obtained by, for example, a solvent extraction method, which is as described in Patent Document 1 (Japanese Unexamined Patent Publication No. Hei8-231410). In addition, cashew nut shell liquid may refer to nut shells and/or cashew nut testa obtained by pulverizing/crushing cashew nut shells, both of which comprise cashew nut shell liquid. The cashew nut testa represents the thin skin between the shell and the germ (nut) of a cashew nut. Moreover, a commercial product of cashew nut shell liquid may be used.

A heated cashew nut shell liquid can be obtained by heating cashew nut shell liquid (unheated) obtained as described above at a temperature of not lower than 70° C. and preferably not lower than 130° C. Alternatively, the cashew nut shell liquid may be a cashew nut shell liquid obtained by storage at room temperature (20° C.) for about one year or longer. The heated cashew nut shell liquid to be used in the present invention may refer to heated nut shells and/or heated cashew nut testa obtained by pulverizing/crushing heated cashew nut shells, both of which comprise cashew nut shell liquid. In poultry (such as chicken), the introduction of some types of antibiotics or feeds may induce symptoms from side effects, such as decreased digestibility, diarrhea, and loss of appetite, and sometimes lead to death. However, the unheated cashew nut shell liquid and heated cashew nut shell liquid are naturally occurring and have no side-effect problems.

The content of cashew nut shell liquid in the productivity enhancing agent and the wasting rate-reducing agent for poultry is preferably from 0.001% by mass to 100% by mass, more preferably from 0.01% by mass to 90% by mass, and further more preferably from 0.1% by mass to 80% by mass. If the content is not less than 0.001% by mass, the given amount of the agent can provide productivity enhancing effects, such as improvement of the maturity rate, improvement of the feed conversion rate, improvement of the production index and reference value, and reduction of the wasting rate due to amelioration of inflammation, colibacillosis, ascites, emaciation and maldevelopment.

When a feed is allowed to contain the productivity enhancing agent or the wasting rate-reducing agent for poultry and the resulting feed is used, the content of cashew nut shell liquid in the feed may be from 0.0001% by mass to 10.0% by mass, preferably from 0.001% by mass to 5.0% by mass, more preferably from 0.001% by mass to 1.0% by mass, further preferably from 0.001% by mass to 0.05% by mass, and particularly preferably 0.001% by mass to 0.1% by mass. If the content is not less than 0.0001% by mass, the given amount of the feed can provide productivity enhancing effects, such as improvement of the maturity rate, improvement of the feed conversion rate, improvement of the production index and reference value, and reduction of the wasting rate due to amelioration of inflammation, colibacillosis, ascites, emaciation and maldevelopment; if the content is not more than 10.0% by mass, the given amount has no effect on the feed composition and, therefore, is preferable. As the cashew nut shell liquid to be used in the present invention, cashew nut shells containing oily substances may be used directly or after pulverizing/crushing the shells, or cashew nut testa may be used, and the content of cashew nut shell liquid in the productivity enhancing agent or the wasting rate-reducing agent, or in the feed may be adjusted within the above-described range in terms of the contained cashew nut shell liquid (CNSL) (CNSL is contained in cashew nut shell in the range of 25 to 30% by mass, while CNSL is contained in cashew nut testa in the range of 0.5 to 3.0% by mass).

If a feed is allowed to contain the productivity enhancing agent or the wasting rate-reducing agent for poultry and the resulting feed is used, it is preferred that a feed for poultry contain cashew nut shell liquid, anacardic acid, cardanol, and/or cardol at a concentration of 1 to 150 ppm and the resulting feed be administered. Preferably, the concentration is from 1 to 100 ppm, and further preferably from 1 to 75 ppm.

The productivity enhancing agent and the wasting rate-reducing agent for poultry according to the present invention may comprise anacardic acid, cardanol, or cardol, instead of cashew nut shell liquid.

Examples of anacardic acid to be used in the present invention include naturally-occurring anacardic acid, synthetic anacardic acid, and derivatives thereof. Moreover, a commercial product of anacardic acid may also be used. Anacardic acid can be obtained as described in Patent Document 1 (Japanese Unexamined Patent Publication No. Hei8-231410) by extracting cashew nut oil from cashew nut shells treated with an organic solvent, subjecting the obtained cashew nut oil to, for example, silica gel column chromatography, and applying a mixture of n-hexane, ethyl acetate and acetic acid with a varying ratio to the chromatography for the elution of the obtained cashew nut oil (see Japanese Unexamined Patent Publication No. Hei3-240721, Japanese Unexamined Patent Publication No. Hei3-240716, etc.). The anacardic acid as described above may be contained in the productivity enhancing agent or the feed to have the similar content as the cashew nut shell liquid.

Examples of cardanol to be used in the present invention include naturally-occurring cardanol, synthetic cardanol, and derivatives thereof. Moreover, cardanol can be obtained by decarboxylation of anacardic acid, a main component of cashew nut shell liquid. The cardanol as described above may be contained in the productivity enhancing agent or the wasting rate-reducing agent, or in the feed to have the similar content as the cashew nut shell liquid.

Examples of cardol to be used in the present invention include naturally-occurring cardol, synthetic cardol, and derivatives thereof. Moreover, cardol can also be obtained from purification of cashew nut shell liquid. The cardol as described above may be contained in the productivity enhancing agent or the wasting rate-reducing agent, or in the feed to have the similar content as the cashew nut shell liquid.

Examples of the poultry to be administered with the productivity enhancing agent and the wasting rate-reducing agent according to the present invention include chickens or quails, and preferably chickens for meat (broiler chickens).

Examples of the chickens for meat include chickens of, for example, White Cornish, White Plymouth Rock, Barred Plymouth Rock, Rhode Island Red, New Hampshire, UK Chunky, US Chunky, Cobb, Avian, Arbor Acres, Hinai-Jidori, Satsuma-Jidori, and Nagoya breeds, and may also include crossbreeds and improved breeds thereof. Among those chicken breeds targeted by the productivity enhancing agent and the wasting rate-reducing agent for chickens for meat according to the present invention, UK Chunky and US Chunky breeds are preferred.

The time point at which the productivity enhancing agent and the wasting rate-reducing agent according to the present invention are administered is not particularly limited, but preferably, the agent is administered to poultry such as chickens for meat at a time point when a feed is switched from a feed for the early fattening phase to a feed for the late fattening phase. For example, unheated cashew nut shell liquid, heated cashew nut shell liquid, anacardic acid, cardanol, and/or cardol are/is preferably fed to poultry such as chickens for meat at their age of one to seven weeks over a period of one to four weeks and further preferably to poultry such as chickens for meat at their age of three to five weeks over a period of one to three weeks.

The productivity enhancing agent and the wasting rate-reducing agent according to the present invention is administered to poultry to reduce the wasting rate of food chickens and thus to enhance the productivity, as compared with those of a non-administration control group which is not administered with unheated cashew nut shell liquid, heated cashew nut shell liquid, anacardic acid, cardanol, and/or cardol, or which is fed with a diet containing none of those components. It is understood that enhancement in productivity is achieved by, for example, individual health promotion, enhanced growth, and increased feed efficiency, while enhancement in productivity can be evaluated, for example, by indices such as improvement of the maturity rate, improvement of the feed conversion rate, improvement of the production index and reference value, and improvement of the wasting rate due to amelioration of inflammation, colibacillosis, ascites, emaciation and maldevelopment. The enhancement in productivity according to the present invention does not include an aspect described in Patent Documents 1 and 2 according to which the productivity is enhanced by amelioration of coccidiosis, an aspect described in WO2010/067883 according to which the productivity is enhanced by amelioration of *Clostridium* infections, and an aspect described in Japanese Unexamined Patent Publication No. 2015-030717 according to which the productivity is enhanced by amelioration of cryptosporidiasis, and further does not include enhancement in productivity by a decreased death rate during molting of egg laying chickens.

As used herein, the term "maturity rate" refers to the ratio of the number of chickens mature enough for shipment to the total number of housed chickens, and is synonymous with "survival rate" and "shipping rate".

As used herein, the term "production score (PS)" represents an economic index indicating the biological productivity of commercial broiler chickens, and is synonymous with "production index". The equation to calculate the production score is as below. An index to evaluate the entire group of chickens is included in the production score, which enables the evaluation of the overall economics.

$$\text{Production score(PS)} = \text{body weight at shipment(g)} \times \text{shipping rate/the number of days of age at shipment/feed conversion rate/10}$$

As used herein, the term "feed conversion rate (FCR)" refers to an index indicating the amount of ingested feed relative to body weight in chickens. For broiler chickens, the efficiency is calculated from the amount of feed required to increase the body weight by 1 kg. The calculation formula is as below. Here, the body weight at shipment is used to calculate the body weight gain.

$$\text{Feed conversion rate} = \text{amount of ingested feed (kg)/body weight gain (kg)}$$

As used herein, the term "colibacillosis" refers to one of the major diseases that bring economic loss in the chicken farming industry, which accounts for about 50% of complete wasting cases determined by the poultry meat inspection and is caused by *Escherichia coli*. The colibacillosis has symptoms such as respiratory symptoms, sepsis, external pericarditis, and arthritis, and exhibits not only digestive system symptoms but also systemic symptoms and thus is different from the "colibacillosis" observed in other farm animals. However, the colibacillosis still has a significant influence on the productivity and can be a cause of wasting by reason of death during the incubation period. Colibacillosis brings about problems such as a decreased maturity rate and an increased wasting rate at the poultry meat inspection, but it is preferred that the techniques presented herein be used to increase the maturity rate and to reduce the wasting rate of poultry meat due to causes including colibacillosis, inflammation, and maldevelopment.

As used herein, the term "inflammation" means inflammation which leads to the wasting of poultry and, according to the law, the visual, tactile and olfactory senses are used to find inflammation at a level that leads to the wasting, which is then confirmed by the presence or absence of histological lesions.

As described above, unheated cashew nut shell liquid, heated cashew nut shell liquid, anacardic acid, cardanol, and/or cardol have/has been shown to be effective in prevention or treatment of colibacillosis or inflammation. Therefore, the present invention provides a prophylactic or therapeutic agent for colibacillosis or inflammation in poultry, which comprises unheated cashew nut shell liquid, heated cashew nut shell liquid, anacardic acid, cardanol, and/or cardol as an active ingredient/active ingredients.

The present invention also provides an ameliorating agent for ascites, emaciation, or maldevelopment in poultry, which comprises unheated cashew nut shell liquid, heated cashew nut shell liquid, anacardic acid, cardanol, and/or cardol as an active ingredient/active ingredients.

If a feed is allowed to contain the prophylactic or therapeutic agent for colibacillosis or inflammation, or the ameliorating agent for ascites, emaciation, or maldevelopment and the resulting feed is used, it is preferred that a feed contain unheated cashew nut shell liquid, heated cashew nut shell liquid, anacardic acid, cardanol, and/or cardol at a concentration of 1 to 150 ppm and the resulting feed be administered. Preferably, the concentration is from 1 to 100 ppm, and further preferably from 1 to 75 ppm. Moreover, the prophylactic or therapeutic agent for colibacillosis or inflammation is preferably administered to poultry such as chickens for meat at their age of one to seven weeks over a period of one to four weeks and further preferably to poultry such as chickens for meat at their age of three to five weeks over a period of one to three weeks.

The dosage forms of the productivity enhancing agent and the wasting rate-reducing agent for poultry, the ameliorating agent for ascites, emaciation, or maldevelopment, and the prophylactic or therapeutic agent for inflammation or colibacillosis in poultry according to the present invention are not particularly limited, but those can be in any dosage form, such as powders, pellets, granules, liquids, solids, tablets, capsules, or emulsions, and can be produced by mixing unheated cashew nut shell liquid, heated cashew nut shell liquid, anacardic acid, cardanol, and/or cardol with any necessary optional components for formulation. In addition, according to a dosage form, cashew nut shell, pulverized/crushed cashew nut shell, or cashew nut testa, each of which contains cashew nut shell liquid, may be used as it is and mixed with any other components to produce the productivity enhancing agent or the prophylactic or therapeutic agent for colibacillosis according to the present invention.

The productivity enhancing agent and the wasting rate-reducing agent for poultry, the ameliorating agent for ascites, emaciation, or maldevelopment, and the prophylactic or therapeutic agent for inflammation or colibacillosis in poultry according to the present invention may be produced as a powder with silica, such as silica with an average diameter of not less than 150 μm, on which unheated cashew nut shell liquid, heated cashew nut shell liquid, anacardic acid, cardanol, and/or cardol are/is adsorbed or contained. Such a silica formulation is described in, for example, WO2009/151048.

The productivity enhancing agent and the wasting rate-reducing agent for poultry, the ameliorating agent for ascites, emaciation, or maldevelopment, and the prophylactic or therapeutic agent for inflammation or colibacillosis in poultry according to the present invention may be agents produced by mixing unheated cashew nut shell liquid, heated cashew nut shell liquid, anacardic acid, cardanol, and/or cardol with an oil absorbing agent such as diatom earth, bentonite, montmorillonite, zeolite, perlite, acid clay, activated clay, or hydrated silica. Such oil absorbing agents are described in, for example, WO2011/013592.

The productivity enhancing agent and the wasting rate-reducing agent for poultry, the ameliorating agent for ascites, emaciation, or maldevelopment, and the prophylactic or therapeutic agent for inflammation or colibacillosis in poultry according to the present invention, each of which comprises unheated cashew nut shell liquid, heated cashew nut shell liquid, anacardic acid, cardanol, and/or cardol, may be mixed with other feed components to be used in foods and supplemental foods for poultry (hereinafter referred to as feed) to produce a feed. The type of the feed and the components other than the active ingredient such as cashew nut shell liquid are not particularly limited, but the feed is preferably a mixed feed composed of cashew nut shell liquid and a feed for the late fattening phase. The feed is for poultry such as chicken. In general, broiler chickens at their age of seven to eight weeks are shipped and processed to meat. It is often the case that, within the duration, a feed for the early fattening phase is provided in the period from the start of feeding to the age of about 21 days and a feed for the late fattening phase is provided thereafter, which means that nutrition plans appropriate for the respective incubation periods are designed. However, this schedule shall not be applied to Jidori breeds which are incubated for a longer period.

The feed of the present invention can be produced by adding the productivity enhancing agent, the wasting rate-reducing agent, the ameliorating agent for ascites, emaciation, or maldevelopment, or the prophylactic or therapeutic agent for inflammation or colibacillosis to feed components and mixing them together. If the productivity enhancing agent, the wasting rate-reducing agent, the ameliorating agent for ascites, emaciation, or maldevelopment, or the prophylactic or therapeutic agent for inflammation or colibacillosis in a powder or solid form is used for the production of the feed, any of the agents may be allowed to temporarily have a liquid or gelatinous form for easy mixing. In this case, water, vegetable oil such as soybean oil, rapeseed oil, and corn oil; liquid animal oil, or water-soluble high molecular compounds such as polyvinyl alcohol, polyvinylpyrrolidone, and polyacrylic acid may be used as a liquid carrier. Moreover, water soluble polysaccharides such as alginic acid, sodium alginate, xanthan gum, sodium caseinate, gum arabic, guar gum, and tamarind seed polysaccharides are also preferably combined in the feed to keep the homogeneity of cashew nut shell liquid.

The feed of the present invention may comprise sugars (such as lactose and trehalose), maize, milo, wheat bran, rice bran, defatted bran, dried bran, steam-rolled barley, steam-rolled corn, soybean cake, corn flour, rice flour, soybean flour and the like. The concentration of these components in the feed is preferably from 1 to 90% by mass, more preferably from 5 to 75% by mass and further preferably from 10 to 50% by mass.

The feed of the present invention may further comprise optional components, such as ingredients effective in growth promotion in poultry such as chickens for meat, nutritional supplements, and ingredients to enhance storage stability. Examples of such optional components include probiotics such as *Enterococcus* bacteria, *Bacillus* bacteria, and *Bifidobacterium* bacteria; enzymes such as amylase and lipase; vitamins such as L-ascorbic acid, choline chloride, inositol, and folic acid; minerals such as potassium chloride, ferric citrate, magnesium oxide, phosphoric acid salts, and zinc sulfate; amino acids such as D,L-alanine, D,L-methionine, and L-lysine hydrochloride; organic acids such as fumaric acid, butyric acid, lactic acid, and acetic acid, and salts thereof; antioxidants such as ethoxyquin and dibutyl hydroxy toluene; fungicides such as calcium propionate; thickeners such as carboxymethyl cellulose (CMC), sodium caseinate, and sodium polyacrylate; emulsifiers such as glycerin fatty acid esters and sorbitan fatty acid esters; pigments such as asthaxanthin and canthaxanthin; and flavors such as various esters, ethers, and ketones.

The feed of the present invention is suitable for rearing poultry such as chickens for meat. The amount of feed to be given can be appropriately adjusted depending on, for example, the breed of chickens, body weight, age, sex, health conditions, and components of the feed, in which unheated cashew nut shell liquid, heated cashew nut shell liquid, anacardic acid, cardanol, and/or cardol contained in the feed is provided in a ratio of preferably 0.001 to 15 grams per chicken per day, more preferably 0.001 to 10 grams per chicken per day and further preferably 0.001 to 5 grams per chicken per day. Routine methods can be used as a feeding method and a rearing method, depending on the breed of chickens.

The examples of the present invention will be described below but the present invention is not limited thereto.

EXAMPLES

Production Example 1

Cashew nut shell liquid (CNSL) was purchased from Thao Nguyen Co., Ltd. The composition of the CNSL was determined by the method below. That is, a HPLC system (Waters 600, Nihon Waters K.K.), a detector (Waters 490E, Nihon Waters K.K.), a printer (Chromatopac C-R6A, Shimadzu Corp.) and a column (SUPELCOSIL LC18, Supelco) were used. A solvent of acetonitrile/water/acetic acid (80: 20:1, vol/vol/vol) and a flow rate of 2 mL/min were used. Detection was performed by absorbance at 280 nm. The cashew nut shell liquid contained 65.7% by mass of anacardic acid, 5.1% by mass of cardanol and 23.5% by mass of cardol.

Example 1

Along with switching to a feed for the late fattening phase, CNSL was started to be added at a ratio of 50 ppm to the feed for the late fattening phase, and the resulting mixed feed was provided to farmed chickens for meat for a duration of two weeks during the period of 21 days to 35 days of age. Operations other than the addition of CNSL are according to the operational procedures commonly performed in the farm where the test has been performed, and the feed for the late fattening phase is a nutrition plan that is high in energy compared to a feed for the initial feeding phase and a feed for the early fattening phase. The shipped test chickens were subjected to a series of poultry meat inspection procedures based on the related laws and regulations, including an antemortem examination, a postmortem examination after defeathering and a postmortem examination after evisceration, according to commonly used procedures at a poultry processing site (Iwate Prefecture).

As a result of the feeding experiment, improvement of the maturity rate (from 94.32 to 96.74%; +2.6%), improvement of the feed conversion rate (from 1.832 to 1.796; −2.0%), and improvement of production score (PS) (from 321.77 to 331.21; +2.9%) were observed in the UK Chunky chickens (50,000 individuals), as shown in Table 1, which indicates enhanced productivity. Also, according to the findings of the later poultry meat inspection, reduced wasting rates were observed in the wasting due to colibacillosis (1.558→0.831%; −44%) and the wasting due to emaciation and maldevelopment (0.288→0.165%; −43%), as shown in Table 2. Particularly, incidence of visceral type of colibacillosis, among other types, was largely decreased from 1.23% to 0.381% (−69%). Accordingly, it was indicated that feeding CNSL greatly contributed to the enhancement of productivity of chickens for meat.

TABLE 1

| | | Feeding group | Control group |
|---|---|---|---|
| Production performance | Number of housed chickens (individuals) | 50,000 | 50,000 |
| | Number of shipped chickens (individuals) | 48,370 | 47,160 |
| | Amount of ingested feed (during the period from the start of feeding to the shipment) (kg) | 5.02 | 5.40 |
| | Maturity rate (%) | 96.74 | 94.32 |
| | Average age (days) | 47.02 | 47.20 |
| | Average body weight (kg) | 2.84 | 2.95 |
| | Feed conversion rate | 1.766 | 1.832 |
| | Daily body weight gain (g) | 60.40 | 62.5 |
| | Production score | 331.21 | 321.77 |

TABLE 2

| | | Feeding group | Control group |
|---|---|---|---|
| Result of the postmortem examination after evisceration | Colibacillosis (%) | 0.871 | 1.558 |
| | Visceral type (%) | 0.381 | 1.230 |
| | Subcutaneous type (%) | 0.490 | 0.328 |
| | Degeneration (%) | 0.155 | 0.116 |
| | Ascites (%) | 0.068 | 0.199 |
| | Wasting and Maldevelopment (%) | 0.165 | 0.288 |
| | Others (%) | 0.159 | 0.120 |
| | Total of rejected chickens (%) | 1.418 | 2.281 |

Example 2

Three days before switching to the feed for the late fattening phase, CNSL was started to be added at a ratio of 100 ppm to the feed, and the resulting mixed feed was provided to farmed chickens for meat for a duration of 17 days during the period of 18 days to 35 days of age. Operations other than the addition of CNSL are according to the operational procedures commonly performed in the farm where the test has been performed, and the feed for the late fattening phase is a nutrition plan that is high in energy compared to a feed for the initial feeding phase and a feed for the early fattening phase. The shipped test chickens were subjected to a series of poultry meat inspection procedures based on the related laws and regulations, including an antemortem examination, a postmortem examination after defeathering and a postmortem examination after evisceration, according to commonly used procedures at a poultry processing site (Miyagi Prefecture). Additionally, colibacillosis was not categorized into inflammation at the above poultry meat inspection site.

As a result of the feeding experiment, nearly unchanged maturity and feed conversion rates, as well as increase of the average body weight (from 2.70 to 2.87; +6.3%), improvement of production score (PS) (from 281.9 to 295.4; +4.8%) were observed in UK Chunky chickens (24,000 individuals), as shown in Table 3, which indicates enhanced productivity. Also, according to the findings of the later poultry meat inspection, the total wasting rate was reduced (from 2.54 to 1.65%; −35%), as shown in Table 4. The wasting due to inflammation and colibacillosis was at a ratio of less than 1% even in a control group, indicating that chickens had been appropriately managed at the above-described farm. On the other hand, a reduced wasting rate was observed in the wasting due to emaciation and maldevelopment (from 1.12 to 0.55%; −51%).

Accordingly, it was indicated that feeding CNSL greatly contributed to the enhancement of productivity of chickens for meat.

TABLE 3

| | | Feeding group | Control group |
|---|---|---|---|
| Production performance | Number of housed chickens (individuals) | 24,720 | 24,205 |
| | Number of shipped chickens (individuals) | 23,657 | 23,092 |
| | Amount of ingested feed (during the period from the start of feeding to the shipment) (kg) | 5.34 | 4.89 |
| | Maturity rate (%) | 95.7 | 95.4 |
| | Average age (days) | 49.2 | 49.2 |
| | Average body weight (kg) | 2.87 | 2.70 |
| | Feed conversion rate | 1.86 | 1.81 |
| | Daily body weight gain (g) | 58.3 | 54.9 |
| | Production score | 295.4 | 281.9 |

TABLE 4

| | | Feeding group | Control group |
|---|---|---|---|
| Result of the postmortem examination after evisceration | Colibacillosis (%) | 0.82 | 0.95 |
| | Inflammation (%) | 0.08 | 0.20 |
| | Ascites (%) | 0.08 | 0.06 |
| | Wasting and Maldevelopment (%) | 0.55 | 1.12 |
| | Others (%) | 0.12 | 0.21 |
| | Total of rejected chickens (%) | 1.65 | 2.54 |

INDUSTRIAL APPLICABILITY

The productivity enhancing agent according to the present invention and the feed comprising the same are useful in the field of chicken farming.

What is claimed is:

1. A method of enhancing productivity of poultry, the method comprising:
   providing the poultry with a feed comprising from 1 to 100 ppm of at least one selected from the group consisting of unheated cashew nut shell liquid, heated cashew nut shell liquid, anacardic acid, cardanol, and cardol, and determining the productivity, thereby enhancing the productivity of poultry,
   wherein the poultry are chickens for meat,
   wherein the productivity is defined as a production score:

Production score (PS)=body weight at shipment (g)× shipping rate/the number of days of age at shipment/feed conversion rate/10, wherein the shipping rate is a ratio of the number of shipped chickens to the total number of housed chickens,
   wherein the feed conversion rate is determined as follows:

Feed conversion rate=amount of ingested feed (kg)/ body weight gain (kg).

2. The method according to claim 1, wherein the chicken for meat is a one- to seven-week-old chicken.

3. The method according to claim 1, wherein the chicken for meat is a three-to five-week-old chicken.

4. The method according to claim 1, wherein the feed is a feed for the late fattening phase.

5. The method of claim 1, wherein the concentration of the at least one selected from the group consisting of unheated cashew nut shell liquid, heated cashew nut shell liquid, anacardic acid, cardanol, and cardol in the feed is from 50 to 100 ppm.

6. The method of claim 1, wherein the feed is fed to the poultry at their age of one to seven weeks over a period of one to four weeks.

7. The method of claim 1, wherein the feed is fed to the poultry at their age of three to five weeks over a period of one to three weeks.

* * * * *